(12) United States Patent
Murakami et al.

(10) Patent No.: US 7,691,054 B2
(45) Date of Patent: Apr. 6, 2010

(54) ENDOSCOPE SYSTEM, TREATMENT INSTRUMENT CARTRIDGE, AND STORAGE CASE

(75) Inventors: Kazushi Murakami, Hino (JP); Takaaki Komiya, Akiruno (JP); Hiroaki Ichikawa, Hachioji (JP); Yoshio Onuki, Hachioji (JP); Yasuhito Kura, Hachioji (JP); Takehiro Nishiie, Akishima (JP); Kazuki Honda, Hachioji (JP)

(73) Assignee: Olympus Medical Systems Corporation, Tokyo (JP)

( * ) Notice: Subject to any disclaimer, the term of this patent is extended or adjusted under 35 U.S.C. 154(b) by 730 days.

(21) Appl. No.: 11/473,815

(22) Filed: Jun. 23, 2006

(65) Prior Publication Data

US 2007/0299304 A1    Dec. 27, 2007

(51) Int. Cl.
A61B 1/00    (2006.01)
(52) U.S. Cl. ................. 600/106; 600/104; 600/131
(58) Field of Classification Search ........... 606/1; 600/101, 102, 104, 106, 120, 131
See application file for complete search history.

(56) References Cited

U.S. PATENT DOCUMENTS

| | | | | |
|---|---|---|---|---|
| 3,835,854 | A * | 9/1974 | Jewett | 604/159 |
| 5,431,645 | A * | 7/1995 | Smith et al. | 606/1 |
| 5,695,491 | A * | 12/1997 | Silverstein | 606/1 |
| 5,931,833 | A * | 8/1999 | Silverstein | 606/1 |
| 5,938,614 | A * | 8/1999 | Sakamoto | 600/104 |
| 6,074,402 | A * | 6/2000 | Peifer et al. | 606/139 |
| 6,171,234 | B1 * | 1/2001 | White et al. | 600/102 |
| 2005/0192475 | A1 * | 9/2005 | Okada | 600/106 |
| 2005/0250989 | A1 * | 11/2005 | Suzuki | 600/106 |
| 2005/0267327 | A1 * | 12/2005 | Iizuka et al. | 600/106 |
| 2005/0288547 | A1 * | 12/2005 | Okada | 600/101 |
| 2006/0094927 | A9 * | 5/2006 | Okada | 600/101 |
| 2007/0185377 | A1 * | 8/2007 | Murakami et al. | 600/106 |

FOREIGN PATENT DOCUMENTS

EP    1 568 306 A1    8/2005

(Continued)

*Primary Examiner*—John P Leubecker
*Assistant Examiner*—Victoria W Chen
(74) *Attorney, Agent, or Firm*—Scully, Scott, Murphy & Presser, P.C.

(57) ABSTRACT

An endoscope system comprises an endoscope, a treatment instrument cartridge, an advancing and retracting device, a controlling device, and an operation instructing device. The endoscope includes a treatment instrument channel in an inserting portion. The treatment instrument cartridge includes a treatment instrument and a storage case. The treatment instrument includes a treatment instrument inserting portion having an elasticity which is inserted through the treatment instrument channel, a treatment section at the tip end thereof, and an operating portion at the base end thereof. The storage case includes an inserting portion storing section into which the treatment instrument inserting portion is wound, an extension port from which the tip end of the wound treatment instrument inserting portion is extended, and a holding section for holding the base end of the treatment instrument inserting portion or the operating portion. The advancing and retracting device has a driving power source and is provided between the treatment instrument inserting channel and the extension port. The controlling device is electrically connected to the driving power source and controls an operation of the driving power source. An operation instructing device issues an instruction on an operation of the driving power source to the controlling device.

17 Claims, 11 Drawing Sheets

FOREIGN PATENT DOCUMENTS

| | | |
|---|---|---|
| EP | 1 602 319 A1 | 12/2005 |
| JP | 08-294545 | 11/1996 |
| JP | 10-085357 | 4/1998 |
| JP | 2004-208961 | 7/2004 |
| JP | 2005-334132 | 12/2005 |
| JP | 08-215338 | 8/2006 |

* cited by examiner

ENDOSCOPE SYSTEM, TREATMENT INSTRUMENT CARTRIDGE, AND STORAGE CASE

BACKGROUND OF THE INVENTION

1. Field of the Invention

The present invention relates to an endoscope system, comprising an endoscope, a treatment instrument used with the endoscope, and a storage case for containing an elongated treatment instrument inserting portion of the treatment instrument.

2. Description of the Related Art

In recent years, an endoscope is widely used in the medical field. An endoscope in the medical field has an inserting portion which is inserted into a body cavity of a subject for observation. The inserting portion of the endoscope is provided with a treatment instrument channel through which a treatment instrument is introduced into the body cavity for various procedures.

When an operator performs a medical procedure by inserting a treatment instrument into a treatment instrument channel of an endoscope, the operator introduces the treatment instrument through the treatment instrument channel into a body cavity. During the introduction, the operator holds the endoscope at its operating portion with one hand. So, in order to insert the treatment instrument through the treatment instrument channel, the operator needs to hold, with the other hand, a sheath which is an introducing section of the treatment instrument, and manually inserts the sheath into the treatment instrument channel. The sheath is held at its base end by a staff such as a nurse. Such holding is necessary to keep a part of the sheath, having a length of 2 m for example, from touching dirty areas including floor during the insertion.

On the other hand, when an operator samples a body tissue for example with a treatment instrument, the operator holds the endoscope at its operating portion with one hand. In this state, the operator cannot operate an operating portion of the treatment instrument with the other hand holding an inserting portion of the endoscope. So a staff holds the endoscope inserting portion, or operates the treatment instrument operating portion.

This means a help by a staff is required in inserting a sheath of a treatment instrument into a treatment instrument channel of an endoscope, and operating the treatment instrument.

For example, Japanese Patent Application Laid-Open No. 2004-208961 discloses an endoscope conduit cleaning apparatus comprising a brush cassette. The endoscope conduit cleaning apparatus has a delivery roller which can be rotated in any direction as needed. An endoscope conduit cleaning brush is contained in a brush cassette in the cleaning apparatus, and the cleaning brush is delivered from a guiding section at a distal end of the cleaning apparatus into an endoscope conduit, and the delivered endoscope conduit cleaning brush can be wound up again to be stored in the brush cassette. However, in the endoscope conduit cleaning apparatus, the brush section can be delivered out and stored in by advancing and retracting a wire, but the wire defines only the forward and backward movement of the brush section.

Japanese Patent Application Laid-Open No. 2005-334132 discloses a treatment instrument for endoscope having a storage device, so-called a drum, which is provided with a rotatable roll member for winding up an inserting portion of an endoscope. In this treatment instrument for endoscope, an operation of a sheath by hand or operation of the drum by hand causes the inserting portion to be delivered and stored. And in this treatment instrument for endoscope, the operating portion of the treatment instrument can be mounted to a side surface of a storage main body. However, because the operations for delivering or winding the sheath cause the operating portion of the treatment instrument at hand to rotate, in order to move the treatment instrument forward or backward during the treatment, the person, that is, an operator or any helper who is operating the treatment instrument, has to release his/her hand from the operating portion, which may be inconvenient.

SUMMARY OF THE INVENTION

An endoscope system according to the present invention comprises an endoscope, a treatment instrument cartridge, an advancing and retracting device, a controlling device, and an operation instructing device. The endoscope includes an inserting portion which has a treatment instrument channel formed therein. The treatment instrument cartridge includes a treatment instrument and a storage case. The treatment instrument has a treatment instrument inserting portion having an elasticity which is inserted through the treatment instrument channel, a treatment section at a tip end of the treatment instrument, an operating portion at a base end of the treatment instrument. The storage case includes an inserting portion storing section for winding up the treatment instrument inserting portion, an extension port from which the tip end of the wound treatment instrument inserting portion is extended, a holding section for holding a part of the treatment instrument inserting portion nearer the base end or the operating portion. The advancing and retracting device has a driving power source, and is displaced between the treatment instrument channel and the extension port. The controlling device is electrically connected to the driving power source, and controls an operation of the driving power source. The operation instructing device issues an instruction on an operation of the driving power source to the controlling device.

The above and other objects, features and advantages of the invention will become more clearly understood from the following description referring to the accompanying drawings.

DETAILED DESCRIPTION OF THE PREFERRED EMBODIMENTS

Now, several embodiments of the present invention will be explained below with reference to accompanying drawings.

Referring to FIGS. 1 to 12, a first embodiment of the present invention will be explained.

Figure 1:
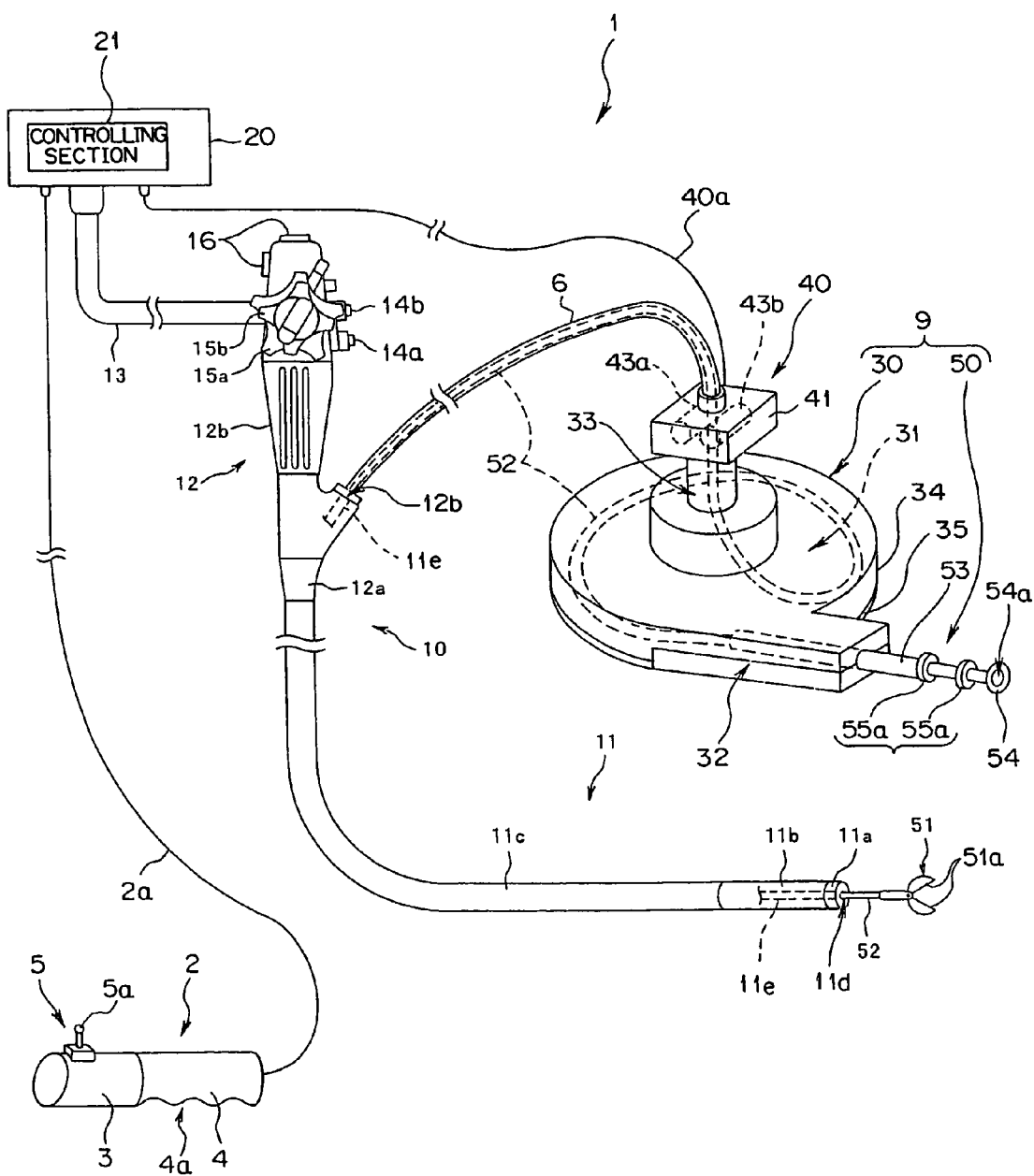
FIG. 1 is a view illustrating an entire configuration of an endoscope system according to a first embodiment.

As shown in FIG. 1, an endoscope system 1 generally comprises an operation instructing device 2, an endoscope 10, a controlling device 20 which serves as a light source device and a video processor, a treatment instrument 50, a storage case (hereinafter, referred to as a case body) 30 in which the sheath 52 which is a treatment instrument inserting portion of the treatment instrument 50 is contained, and an electric device for advancing and retracting a treatment instrument inserting portion (hereinafter, referred to as an electric advancing and retracting device) 40 which is an advancing and retracting device. It should be noted that in this embodiment, a treatment instrument cartridge 9 is comprised with the case body 30 which contains at least the treatment instrument inserting portion of the treatment instrument 50.

The operation instructing device 2 is of a generally cylindrical shape, and includes a rigid main body 3, and a grip 4 which may be an elastic member coupled to the main body 3. The main body 3 and the grip 4 are integrally formed as a unit by fitting a fitting projection (not shown) which extends from a central portion of a base end surface of the main body 3 into a fitting hole (not shown) which is formed in a tip end surface of the grip 4. A signal cable 2a extends from a base end of the grip 4. The signal cable 2a is electrically connected to the controlling device 20 at a base end thereof.

The main body 3 has a circumferential surface on which an operation instructing section 5 is provided. On the other hand, the grip 4 includes a grip section 4a which has a concavo-convex profile. This profile allows an operator to hold the operation instructing device 2 without fail when the operator holds the grip section 4a. The grip section 4a is provided on the other side of circumferential surface of the grip 4 relative to the operation instructing section 5 of the main body 3.

As for the operation instructing device 2 configured in this way, in the following description, a tip end of the operation instructing device 2 means the tip end surface of the main body 3, and a base end of the operation instructing device 2 means the base end surface of the grip 4.

The operation instructing section 5 may be a joy stick type of operation lever 5a, for example. When an operator pushes the operation lever 5a toward the tip end of the operation instructing device 2, an instruction signal to cause the sheath 52 to be advanced is output from the operation instructing section 5 to the control section 21 of the controlling device 20. In addition, when an operator pulls the operation lever 5a toward the base end of the operation instructing device 2, an instruction signal to cause the sheath 52 to be retracted is output from the operation instructing section 5 to the control section 21 of the controlling device 20.

The endoscope 10 comprises an inserting portion 11, and an operating portion 12, and a universal cord 13. The operating portion 12 also serves as a holding section, and is provided at a base end of the inserting portion 11. The universal cord 13 extends from a side of the operating portion 12 to be connected to the controlling device 20 at a base end thereof.

The inserting portion 11 comprises, in order from a tip end thereof, a rigid tip end section 11a, a bendable bending section 11b, and a flexible tube section 11c having a flexibility. The tip end section 11a has a tip end opening 11d formed therein. The operating portion 12 is provided with a protection hood portion 12a having a base end of the flexible tube section 11a connected thereto. The operating portion 12 includes an opening for treatment instrument 12b at its tip end, and includes an air/water supplying button 14a for supplying air/water, a suction button 14b for suctioning, bending control knobs 15a and 15b for controlling the bending of the bending section 11b, and various switches 16 for controlling endoscope images which are caught by an image capturing device at the tip end 11a at its base end.

It should be noted that the inserting portion 11 of the endoscope 10 also includes a treatment instrument channel 11e which is in communication between the opening for treatment instrument 12b and the tip end opening 11d.

The controlling device 20 includes the control section 21, a lamp which emitting an illumination light (not shown), a signal processing circuit (not shown), and the like. The signal processing circuit generates a driving signal to drive an image capturing device such as CCD (not shown) which is located to the tip end of the endoscope, converts an electrical signal transmitted from the image capturing device into an image signal, and the like. The controlling device 20 is connected with a displaying apparatus such as a liquid crystal display (not shown) for displaying an endoscope image.

The treatment instrument 50 may be for example a biopsy forceps (hereinafter, referred to as a biopsy forceps 50), and includes a sheath 52 which is a flexible tube member having a predetermined flexibility. The sheath 52 includes a tissue sampling section 51 at a tip end side of a tip end 52a thereof as a treatment section. The tissue sampling section 51 includes a pair of closable and openable biopsy cups. Through the sheath 52 of the biopsy forceps 50, an operation wire (not shown) is inserted. The operation wire is controlled to be advanced or retracted by an operation of a handle section 53. And the advancement or retraction of the operation wire corresponding to an operation of a handle section 53 causes the tissue sampling section 51 to move from its open position to its closed position, and vice versa. The handle section 53 includes a finger engaging ring 54 and a slider 55. The finger engaging ring 54 has a hole 54a formed therein to which an operator's thumb for example may be engaged. The slider 55 has a pair of flanges 55a to which an operator's second and third fingers may be engaged.

The case body 30 is a storage case for containing the sheath 52 therein, and includes a sheath storing section 31, a treatment instrument holding section 32, and a sheath extracting section 33. The sheath storing section 31 is a storing space in which a sheath 52 is contained.

Specifically, the sheath storing section 31 is configured with a first member 34 having a recess for the storing space (which is designated 38c in FIG. 7 described below) and a second member 35 disposed to cover an opening of the recess, which are integrally fixed to each other.

The treatment instrument holding section 32 has a handle mounting hole 32a formed therein, in which the handle section 53 of the biopsy forceps 50 is mounted. The handle mounting hole 32a is a second through-hole which defines a direction in which a part of the sheath 52 nearer at the base end 52b is extracted as predetermined, and is configured to serve as a second defining section.

A sheath extracting section 33 is provided at the center of the first member 34 as a projected portion. The sheath extracting section 33 has an extracting hole 33a formed therein. The extracting hole 33a is an extension port to which the stored sheath 52 in the storing space is extracted out of the case body 30. In other words, the extracting hole 33a is a first through-hole constituting an insertion port, and is configured to serve as a first defining section.

Figure 5:
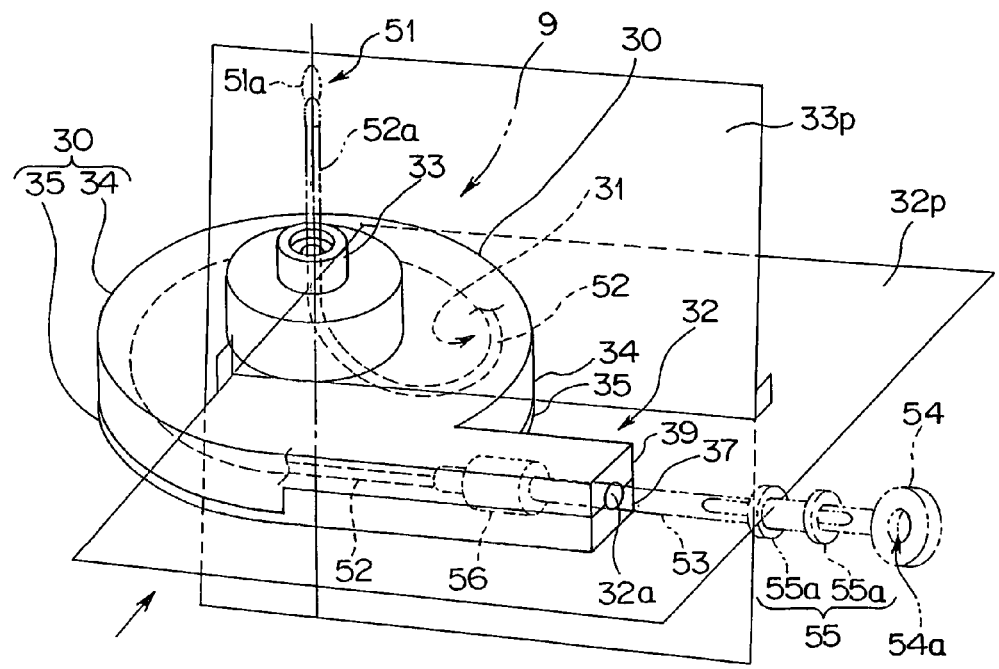
FIG. 5 is a perspective view illustrating a configuration of a storage case, and a perspective view illustrating a treatment instrument cartridge.

In this embodiment, the extracting hole 33a and the handle mounting hole 32a in the case body 30 are provided so that, as shown in FIG. 5, a plane 33P including the central axis of the extracting hole 33a and the plane 32P including the central axis of the handle mounting hole 32a intersect with each other at a right angle, while the central axis of the extracting hole 33a and the central axis of the handle mounting hole 32a do not intersect with each other.

This means the central axis of the extracting hole 33a does not intersect with the central axis of the handle mounting hole 32a, but intersects with a guiding plane 36a at a generally right angle, while the central axis of the handle mounting hole 32a is parallel to the guiding plane 36a. Thus, the sheath extracting section 33 is mounted at a right angle relative to the guiding plane 36a. The treatment instrument holding section 32 is mounted parallel to the guiding plane 36a. It should be noted that in this configuration, the central axis of the extracting hole 33a and the central axis of the handle mounting hole 32a do not intersect with each other.

Figure 6:
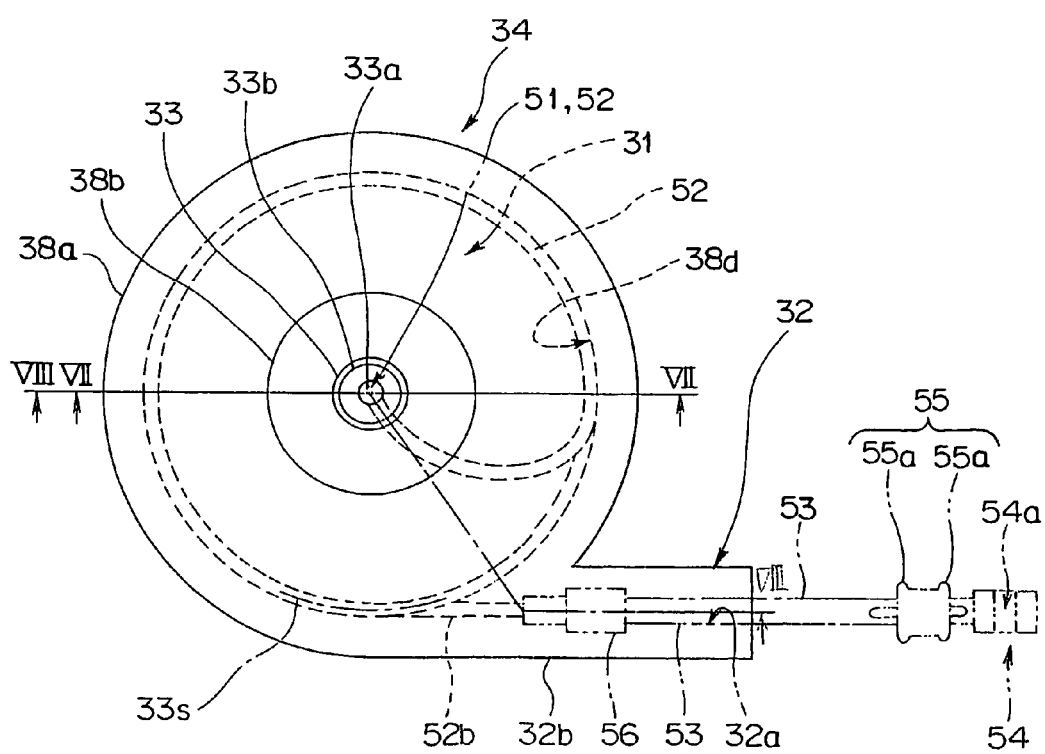
FIG. 6 is a top plan view showing the storage case and the treatment instrument cartridge of FIG. 4.

In addition, in this embodiment, the central axis of the handle mounting hole 32a is a line tangent to an imaginary circle 33S around a point at the intersection of the central axis of the extracting hole 33a on the guiding plane 36a, as shown by two-dot chain line in FIG. 6. Therefore, when the case body 30 is seen from the direction shown by an arrow in FIG. 5, the central axis of the extracting hole 33a and the central axis of the handle mounting hole 32a intersect with each other at a right angle.

The electric advancing and retracting device 40 is removably mounted to sheath extracting section 33 of the case body 30. The electric advancing and retracting device 40 is electrically connected to the controlling device 20 via an electrical cable 40a in which a signal line is inserted. The electric advancing and retracting device 40 causes the sheath 52 of the biopsy forceps 50 to be advanced or retracted based on an operation of the operation lever 5a on the operation instructing device 2.

It should be noted that reference numeral 6 designates a coupling tube. The coupling tube 6 has one end which is mounted to the opening for treatment instrument 12b, and the other end mounted to the electric advancing and retracting device 40. Therefore, the sheath 52 extracted out of the case body 30 is introduced into the treatment instrument channel 11e via the coupling tube 6.

Now, referring to FIG. 1, FIG. 2, and FIG. 3, the electric advancing and retracting device 40 will be explained below.

Figure 2:
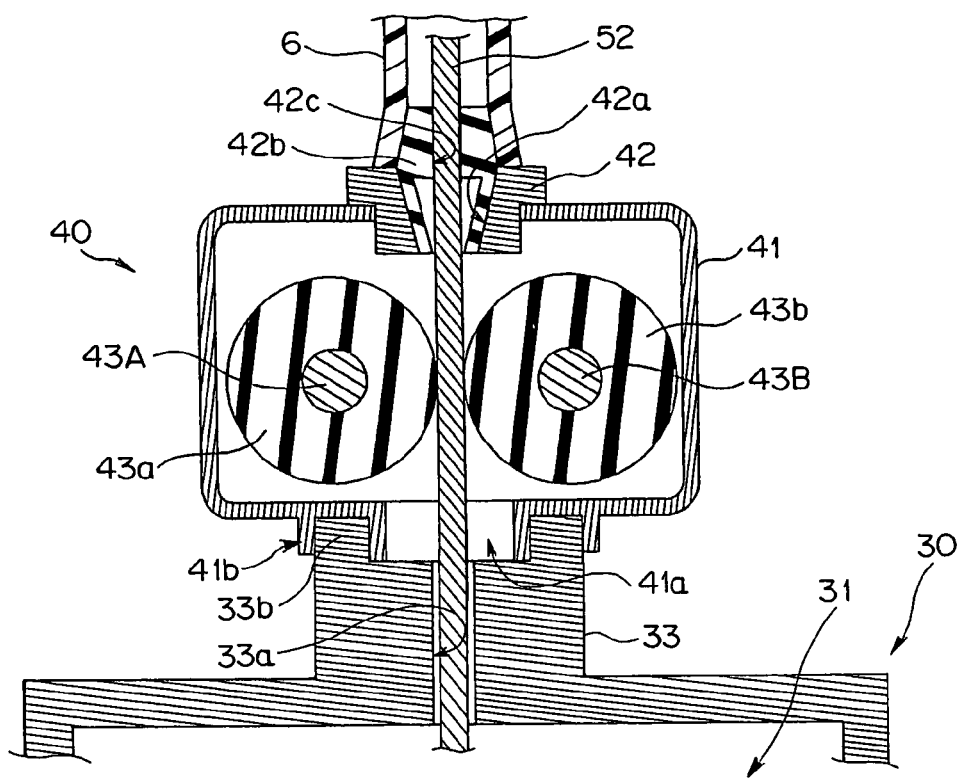
FIG. 2 is a longitudinal cross sectional view showing an internal configuration of an electric advancing and retracting device.

As shown in FIG. 2, the sheath extracting section 33 has an extracting hole 33a which is in communication between the exterior and the inside of the sheath storing section 31. The sheath extracting section 33 includes a mounting section 33b on which the electric advancing and retracting device 40 is mounted.

Figure 3:
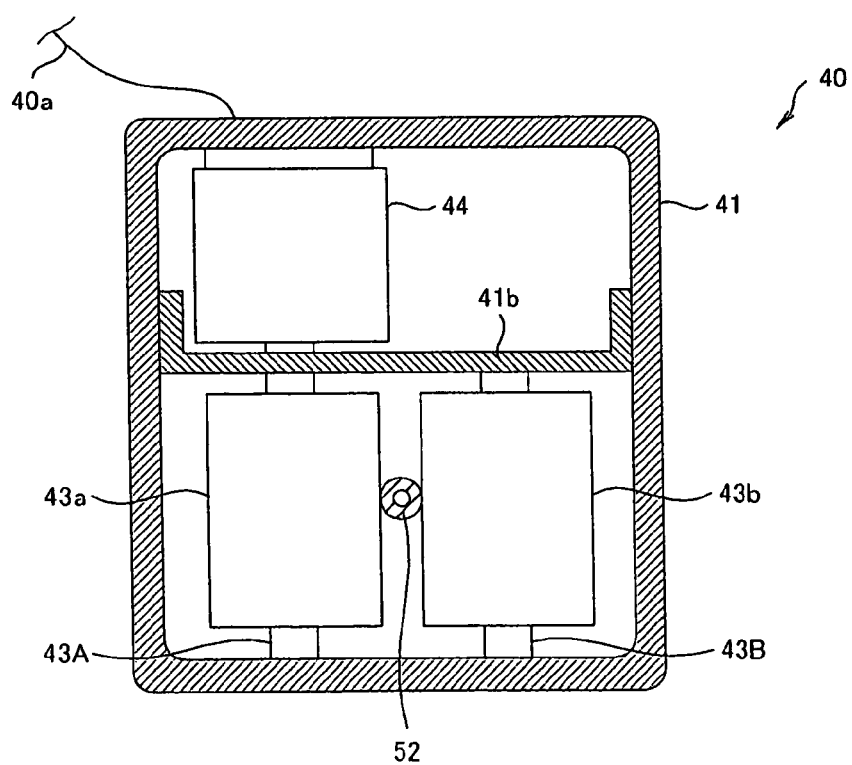
FIG. 3 is a lateral cross sectional view showing an internal configuration of an electric advancing and retracting device.

As shown in FIG. 1, FIG. 2, and FIG. 3, the electric advancing and retracting device 40 has a housing 41 which is provided with two rotatable rollers 43a and 43b therein. The housing 41 includes surfaces facing each other, and one of the surfaces has a sheath inserting hole 41a formed therein through which the sheath 52 passes after extracted out of the sheath extracting section 33. Surrounded the sheath inserting hole 41a is a couplable fixing section 41b for coupling the housing 41 to a mounting section 33b. The couplable fixing section 41b is configured to be hermetically connected to the mounting section 33b.

The other surface of the housing 41 has a treatment instrument inserting portion 42 formed therein through which the sheath 52 is inserted after passed the sheath inserting hole 41a. The treatment instrument inserting portion 42 has a communicating hole 42a formed therein into which a forceps plug 42b of an elastic material is placed. The forceps plug 42b has a slit 42c formed therein through which the sheath 52 is inserted.

The two rollers 43a and 43b in the housing 41 are made of a resin material having an elasticity respectively. The rollers 43a and 43b are integrally fixed to rotation axes 43A and 43B thereof respectively. The sheath 52, which is inserted in the housing 41 after passed the sheath inserting hole 41a, is displaced between the roller 43a and the roller 43b. This arrangement makes the outer surface of the sheath 52 pressed and held between the roller 43a and the roller 43b. The rotation axis 43A is a driving axis, and an operation of a motor 44 which is a driving power source mounted in the housing 41 causes the rotation axis 43A to be rotated. To the contrary, the rotation axis 43B is a driven axis which is rotatably mounted in the housing 41.

In the above-described configuration, an operation of the motor 44 allows the sheath 52 which is held between the roller 43a and the roller 43b to be moved corresponding to the rotation of the roller 43a. That is, the sheath 52 is advanced or retracted in the treatment instrument channel 11e by controlling the direction in which the motor 44 is driven to rotate. The motor 44 is controlled to be driven by the control section 21 of the controlling device 20 based on an operation of the operation lever 5a.

It should be noted that the rotation axes 43A and 43B are rotatably supported by side walls of the housing 41 and a supporting plate 41c so that the rotation axes 43A and 43B are parallel to each other and roller surfaces of the rollers 43a and 43b which are fixedly mounted to the rotation axes 43A and 43B respectively are separated across a predetermined space.

Now, referring to FIG. 1 and FIGS. 4 to 7, a relationship between the case body 30 and the treatment instrument 50 will be explained below.

Figure 4:
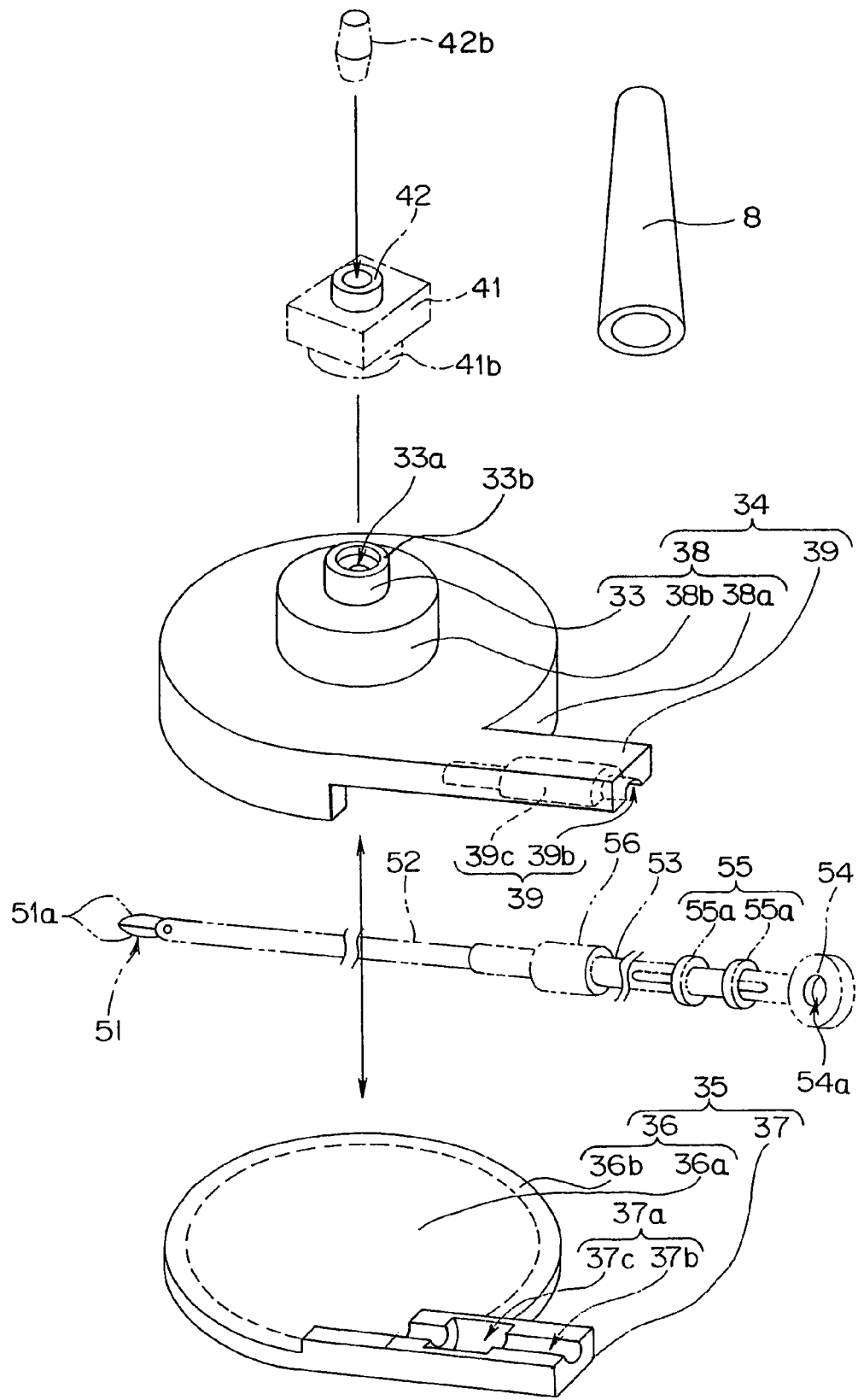
FIG. 4 is an exploded perspective view illustrating a storage case and a treatment instrument of a treatment instrument cartridge, and an electric advancing and retracting device.

As shown in FIG. 4 and FIG. 5, the case body 30 may be, for example, divided into two portions of the first member 34 and the second member 35. The dividing surfaces between the first member 34 and the second member 35 are integrally fixed to each other by adhering, fusion bonding, or the like. At least one of the first member 34 and the second member 35 of the case body 30 is desirably made of a transparent or semi-transparent resin material. This allows an operator to visually check a state of the sheath 52 stored in the sheath storing section 31 through the first member 34 or the second member 35.

The second member 35 includes a flat plate 36 and a second holding section component 37. The flat plate 36 may be of a circular shape, and one part of the flat plate 36 is a guiding plane 36a against which the sheath 52 abuts. It should be noted that an outer peripheral portion surrounding the guiding plane 36a is the above-described dividing surface and also a placement surface 36b on which the first member 34 is placed. The shape of the flat plate is not limited to a circle, and the flat plate 36 may be of any shape including polygonal shapes such as regular tetragon and regular hexagon.

The second holding section component 37 is of a generally rectangular parallelepiped shape, and has a thickness which is larger than that of the flat plate 36 by a predetermined amount in consideration of the diameter of the handle section 53 of the biopsy forceps 50. The second holding section component 37 has one side surface 32b which is configured to be positioned generally tangent to the outer circumference of the flat plate 36 when the treatment instrument holding section 32 is assembled as shown in FIG. 6.

The second holding section component 37 has a handle mounting groove 37a to form the handle mounting hole 32a in which the handle section 53 is mounted at side of the dividing surface.

The handle mounting groove 37a includes a handle resting groove 37b and groove for rotatable holding 37c. In the groove for rotatable holding 37c is placed a projection 56 on the handle section 53. The groove for rotatable holding 37c prevents the handle section 53 from dropping off in a longitudinal axial direction of the treatment instrument holding section 32. The handle mounting groove 37a has a dimension larger than the outer dimension of the handle section 53 so that the handle section 53 can be fitted in the groove for rotatable holding 37c with a play between the handle section 53 and the groove for rotatable holding 37c. This allows the handle section 53 to be rotatably placed relative to the treatment instrument holding section 32. It should be noted that, if the handle section 53 has a recess instead of the projection 56, the handle mounting groove 37a is provided with a projection for rotatable holding instead of the groove for rotatable holding 37c.

Meanwhile, the first member 34 includes a tubular member 38 and a first holding section component 39. The tubular member 38 is formed into a stepped shape, and has a storage space defining section 38a having a larger diameter, an extracted shape adjusting section 38b having a smaller diameter than that of the storage space defining section 38a, and the sheath extracting section 33 having a smaller diameter than that of the extracted shape adjusting section 38b. The storage space defining section 38a has a generally same outline shape as that of the flat plate 36. In this embodiment, the storage space defining section 38a, the extracted shape adjusting section 38b and the sheath extracting section 33 are concentrically arranged. The extracting hole 33a is positioned centrally of the sheath extracting section 33.

Figure 7:
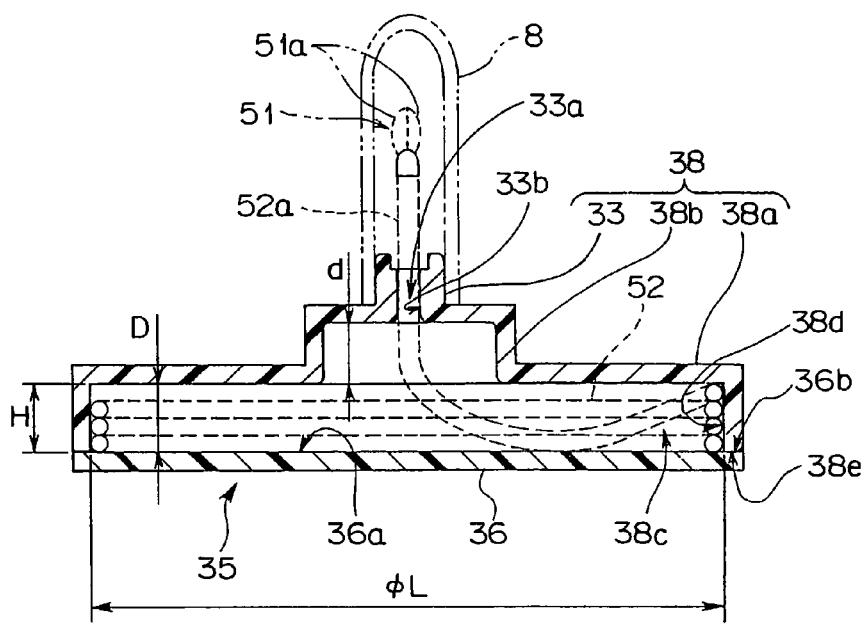
FIG. 7 is a cross sectional view taken along the VII-VII line in FIG. 6.
Figure 8:
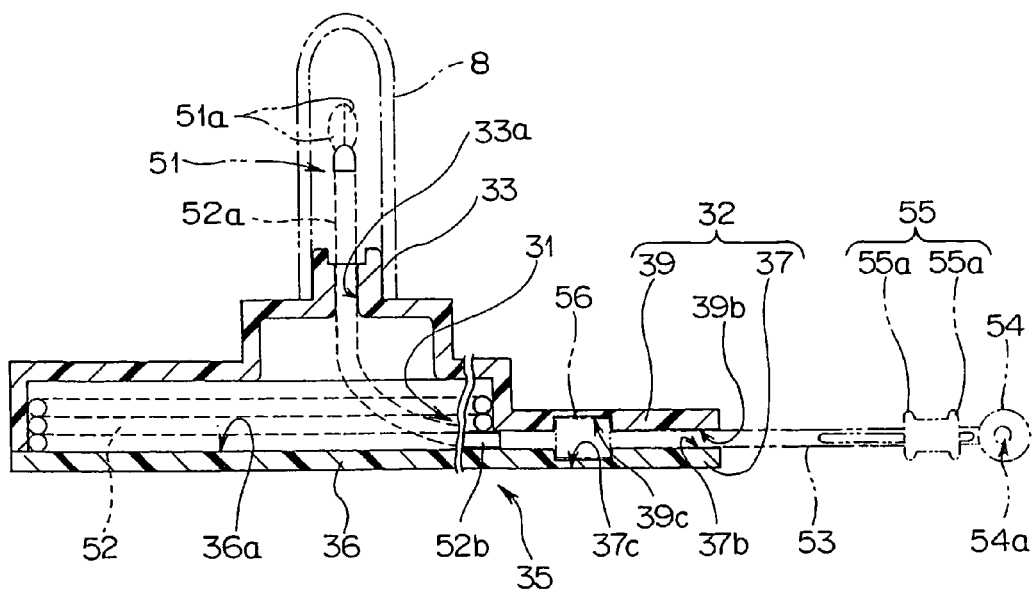
FIG. 8 is a cross sectional view taken along the VIII-VIII line in FIG. 6.

The storage space defining section 38a is an inserting portion storing section, and as shown in FIG. 7 and FIG. 8, is provided with a recess 38c for a sheath storing section 31. The recess 38c has a storage surface 38d which is the internal surface of the recess 38c, and the sheath 52 is stored in the recess 38c in contact with the storage surface 38d. So, the diameter φL of the recess 38c, that is the internal dimension of the recess 38c, is determined in consideration of a repulsion, so-called elasticity and a length of the sheath 52 of the biopsy forceps 50.

Since the internal dimension of the recess 38c is determined in consideration of an elasticity of the sheath 52 as described above, when the sheath 52 is wound and stored in the recess 38c, the elasticity of sheath 52 makes the sheath 52 unwound and stretched outward in a direction in which the winding of the sheath 52 is released, resulting in that the sheath 52 is pushed against the storage surface 38d to be in contact with the storage surface 38d.

The recess 38c has a depth D which is determined in consideration of a diameter and a length of the sheath 52. Specifically, with the wound and laminated sheath 52 in contact with the storage surface 38d of the recess 38c, there is a relationship between a height H of the wound sheath and the depth D as follows:

$$H < D \text{ and } D \approx H$$

This relationship allows the sheath 52, contained in the recess 38c after wound up, to be stably stored in the recess 38c of the sheath storing section 31 with being in a close contact with the storage surface 38d.

The extracted shape adjusting section 38b has a depth d which is determined in consideration of a repulsion of the sheath 52. A specific depth d is set so that, with the sheath 52 being wound and laminated in the sheath storing section 31, when the sheath 52 at the top layer contacts the guiding plane 36a and reaches the extracting hole 33a, the sheath 52 near the extracting hole 33a has a shape (hereinafter, referred to as an extracted shape) of a curved line having a gentle radius of curvature. In other words, the extracted shape adjusting section 38b is provided to prevent any bending of the wound sheath 52 while being advanced to the extracting hole 33a.

It should be noted that, if an inner dimension is set to be larger relative to the sheath length, the sheath 52 can have an extracted shape of gently curved line without the extracted shape adjusting section 38b. This eliminates the extracted shape adjusting section 38b, and the first member 34 includes only the sheath extracting section 33. Reference numeral 38e designates a contact surface disposed on the placement surface 36b.

As shown in FIG. 4 and FIG. 5, the first holding section component 39 is of a generally rectangular parallelepiped shape similar to that of the second holding section component 37. The first holding section component 39 has a handle mounting groove 39a formed on the dividing surface side to form the handle mounting hole 32a in which the handle section 53 of the biopsy forceps 50 is mounted. The handle mounting groove 39a is configured in the same way as the handle mounting groove 37a in the second holding section component 37, and has a handle mounting groove 39b and a groove for rotatable holding 39c having a configuration similar to that in the second holding section component 37 respectively.

Now, steps of a procedure to assemble the treatment instrument cartridge 9 by containing the sheath 52 of the biopsy forceps 50 into the case body 30 will be explained below.

First, a worker assembling the cartridge sterilizes and prepares the biopsy forceps 50, the first member 34, the second member 35 for the case body 30, and the like.

Figure 9:
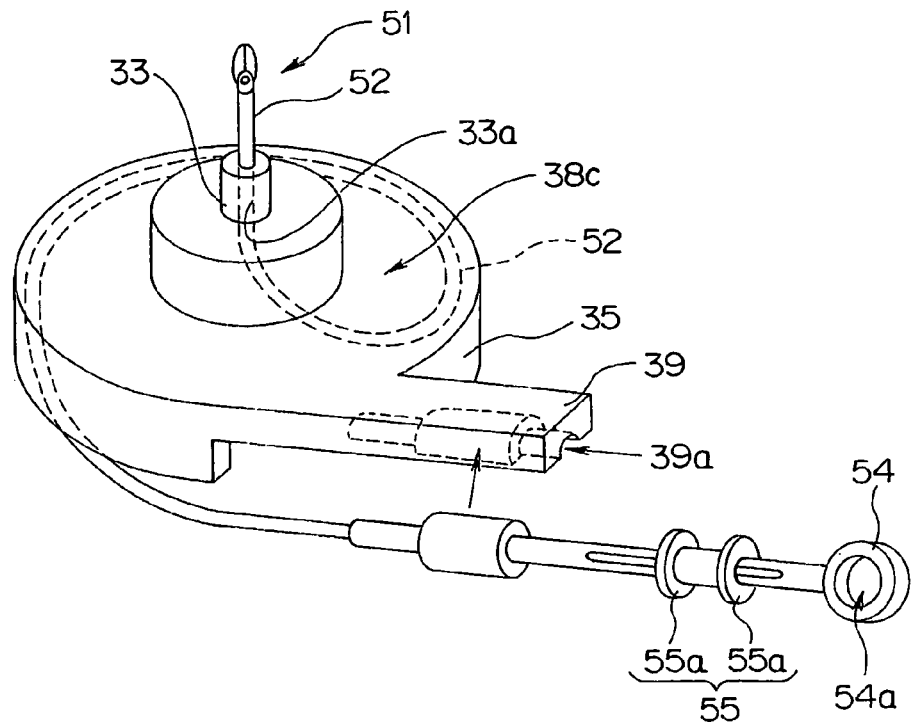
FIG. 9 is a view illustrating an arrangement of a treatment instrument in a storage case.

Next, the worker, as shown in FIG. 9, extracts the tip end 52a of the sheath 52, where the tissue sampling section 51 of the biopsy forceps 50 is located, outward through the extracting hole 33a from the side of the recess 38c of the tubular member 38. Then the worker winds up the sheath 52 of the biopsy forceps 50, and puts the sheath 52 into the recess 38c with the elasticity of the sheath 52 which pushes the sheath 52 against the storage surface 38d of the recess 38c, and places the handle section 53 into the handle mounting groove 39a.

Then, the worker places the second member 35 with respect to the first member 34 in a predetermined way. That is, the worker places the placement surface 36b to the contact surface 38e in a predetermined way. The worker integrally fixes the first member 34 and the second member 35, for example by using an adhesive. Then, the case body 30 including the sheath storing section 31 and the treatment instrument holding section 32, as shown in FIG. 1, FIG. 5, and FIG. 6, is assembled.

As shown in FIG. 1, FIG. 7, and FIG. 8, the sheath 52 is wound in layers, and stored in the case body 30 with being pressed against the storage surface 38d which extends in a vertical direction from the guiding plane 36a of the sheath storing section 31 of the case body 30.

As shown in FIG. 6 and FIG. 8, in the treatment instrument cartridge 9, the tip end 52a of the sheath 52 is placed centrally of the case body 30. While, the base end 52b of the sheath 52 located near the handle section 53 is placed in contact with the storage surface 38d and the guiding plane 36a, and the middle part of the sheath 52 is wound up in close contact with the storage surface 38d.

The sheath 52, which is wound in layers, contacts the guiding plane 36a at the top layer position, and then is extended outward through the extracting hole 33a. Upon the extension, in the sheath storing section 31, the sheath part 52, which extends downward from the storage side opening of the extracting hole 33a to contact once the guiding plane 36a and then extends upward to the storage surface 38d, forms an extracted shape of a gentle radius of curvature 52R.

It should be noted that the curved shape of the curvature is determined by the positions of the extracting hole 33a and the handle mounting hole 32a, and the radius of the curvature 52R changes depending on an elasticity of the sheath 52 and an inner dimension and a depth D of the recess 38c.

In this embodiment, the dividing surfaces are integrally fixed by adhering or fusion bonding. However, the configuration of the case body 30 in not limited to this, and the first member 34 and the second member 35 may be integrally fixed by using a fastening member such as a screw. In this case, for example, an O ring may be provided to the dividing surfaces as a watertight member to obtain a hermetically fixed configuration. An O ring may be provided even when the dividing surfaces are integrally fixed by adhering or fusion bonding, in order to obtain watertightness.

Figure 10:
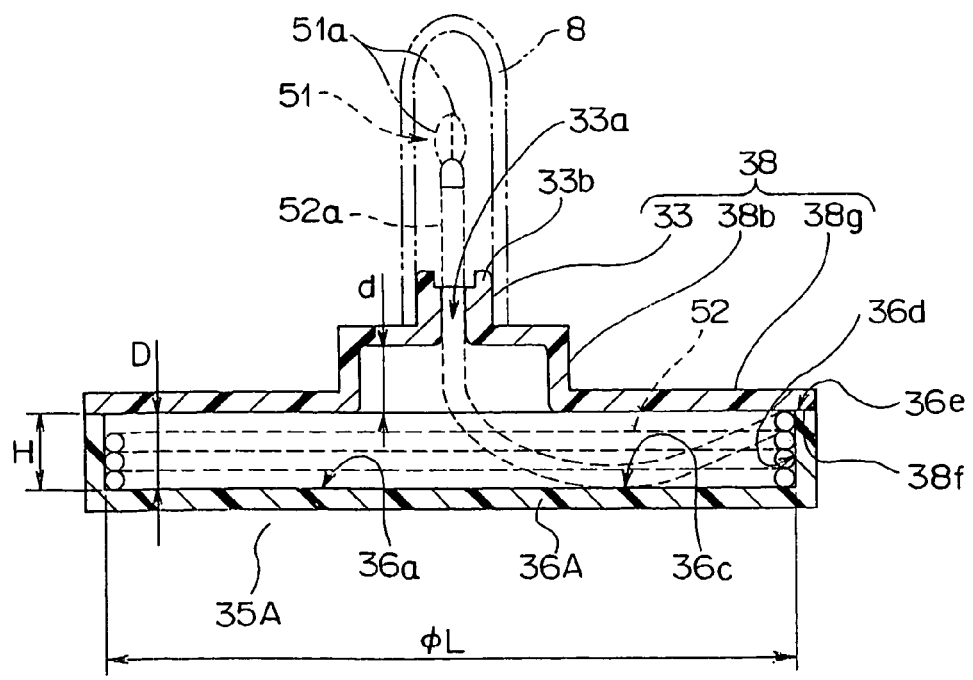
FIG. 10 is a view showing an exemplary configuration of a storage case having a different dividing plane.

In this embodiment, the first member 34 has a recess 38c to form the case body 30. However, as shown in FIG. 10, the second member 35A may have a recess 36c.

In this configuration, the second member 35A includes a guiding plane 36a, a tubular member 36A having a recess 36c, and a second holding section component (not shown) which is configured in the same way as the first holding section component. The recess 36c has a storage surface 36d which is the internal surface of the recess 36c and extends in a vertical direction from the guiding plane 36a.

To the contrary, the first member 34A is formed into a tubular member 38A which includes a flat plate 38g having a resting surface 38f instead of the storage space defining section 38a having the recess 38c, the extracted shape adjusting section 38b, and the sheath extracting section 33. Onto the resting surface 38f, a contact surface 36e located at a tip end of the tubular member 36A is placed to be integrally fixed, resulting in a formed sheath storing section.

Not shown, but each of the first member and second member may have a recess so that the recesses in each member can be combined to form a sheath storing section.

Now, operations of the treatment instrument cartridge 9 configured in the way described above will be explained below.

First, movements of the sheath 52 in the sheath storing section 31, when the sheath 52 which is wound and contained in the sheath storing section 31 is extracted through the extracting hole 33a, will be explained.

Figure 11A:
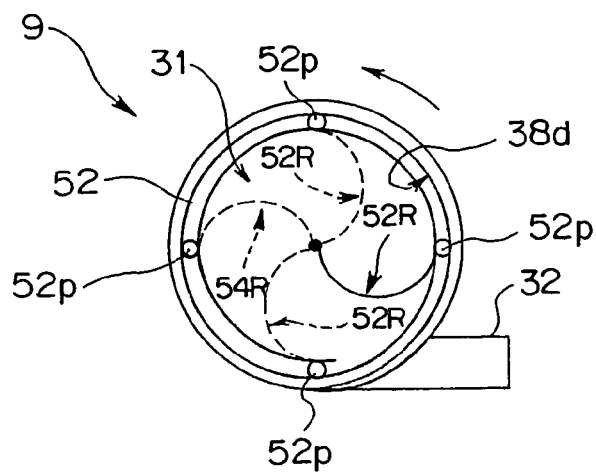
FIG. 11A is a view illustrating a state in which a wound sheath in a storage case is about to be extracted out.

As shown in FIG. 5, the projected sheath 52 is extracted through the extracting hole 33a. As the sheath 52 is extracted outward, as shown in FIG. 11A, a guiding position 52p which moves from the storage surface 38d toward the guiding plane 36a moves counterclockwise from the position shown by a solid line, as shown by an arrow. As the sheath 52 is extracted outward, the layers of the sheath 52 are decreased. During the extraction, the sheath 52 is placed in contact with the storage surface 38d due to the elasticity of the sheath 52. So the extracted shape of the sheath 52 has a curvature 52R having a shape shown by the solid line which is generally similar to that when the wound sheath 52 is contained in the sheath storing section 31. After the sheath 52 is further extracted, the bottom layer of the sheath 52, that is, a part of the sheath 52 which is placed on the guiding plane 36a in contact with the storage surface 38d, is finally to be extracted.

Figure 11B:
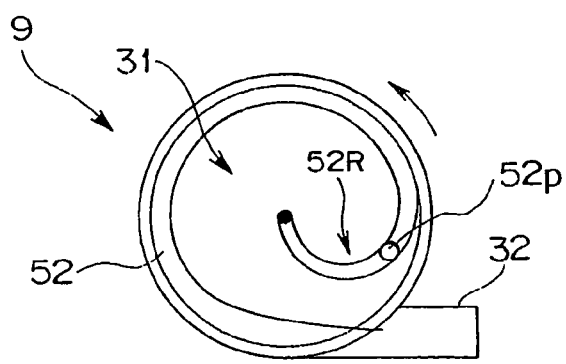
FIG. 11B is a view illustrating a state in which the sheath disposed on a guiding plane of the storage case is being extracted out.
Figure 11C:
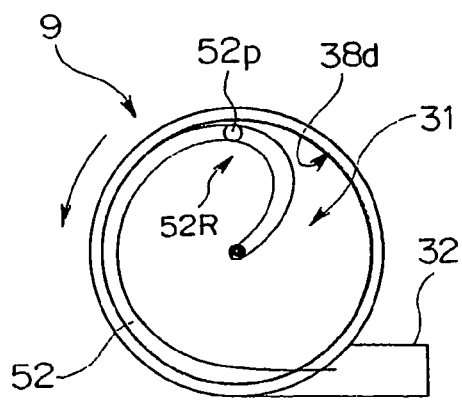
FIG. 11C is a view illustrating a state in which the sheath disposed on a guiding plane of the storage case is further extracted out.
Figure 11D:
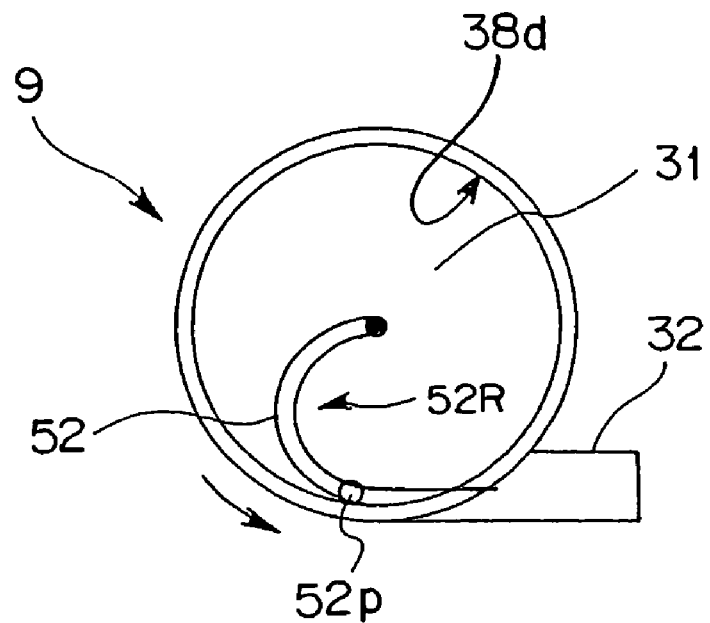
FIG. 11D is a view illustrating a state in which the sheath disposed on a guiding plane of the storage case is even further extracted out.
Figure 11E:
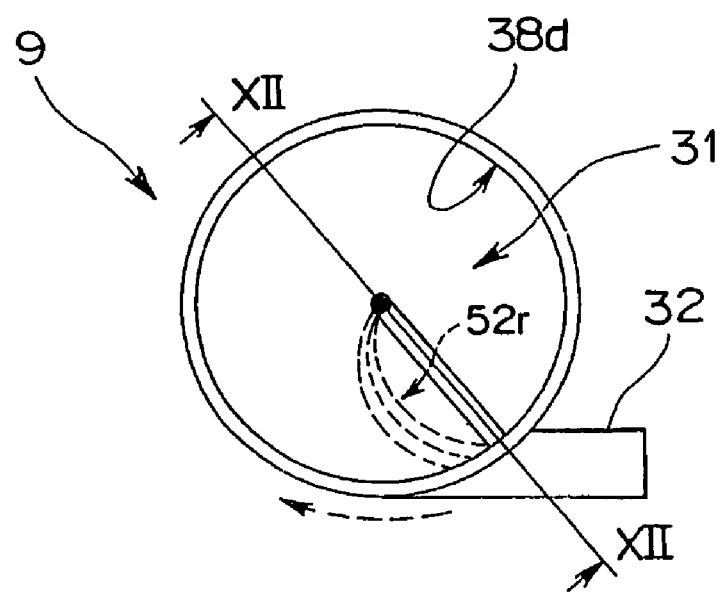
FIG. 11E is a view showing a state in which the entire sheath in the storage case is extracted out.
Figure 12:
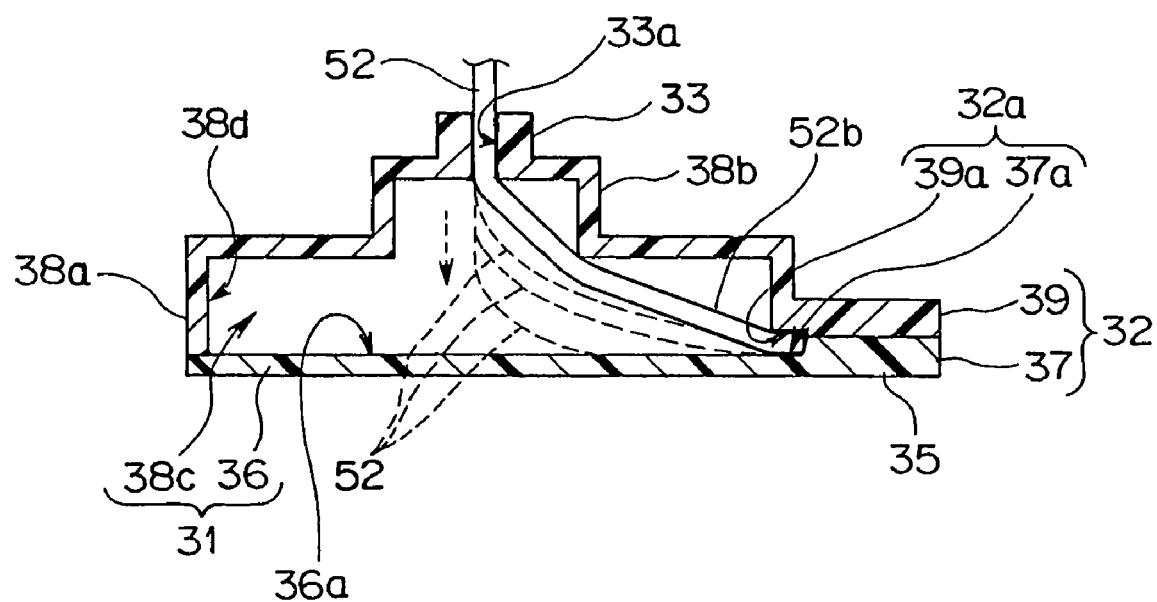
FIG. 12 is a cross sectional view taken along the XII-XII line in FIG. 11E.

The sheath 52 is continuously further extracted. Then, as shown in FIG. 11B, FIG. 11C, and FIG. 11D, with the curvature 52R being maintained in the generally similar shape, the guiding position 52p moves counterclockwise as shown by an arrow as described above. In this way, the entire sheath 52 in the sheath storing section 31 is extracted. At this point, a part of the sheath 52 which extends from the handle section 53 in the handle mounting hole 32a and directs toward the extracting hole 33a has a generally linear extracted shape, as shown in FIG. 11E and FIG. 12.

Next, movements of the sheath 52 in the sheath storing section 31, when the sheath 52 which is once extracted out of the sheath storing section 3 is again received in the sheath storing section 31 of the treatment instrument cartridge 9, will be explained.

A receipt of the sheath 52 into the sheath storing section 31 is started. As shown by a dotted line in FIG. 12, a part of the sheath 52 nearer the base end thereof moves toward the guiding plane 36a little by little. As the sheath 52 moves, as shown by a dotted line in FIG. 11E and FIG. 12, the linear shape of the sheath 52 changes into a curvature 52r. This means, as the more sheath 52 is contained in the sheath storing section 31, a part of the sheath 52 nearer the base end thereof is brought in contact with the storage surface 38d and the guiding plane 36a due to its elasticity and the like.

As the more sheath 52 is contained in the sheath storing section 31, the sheath 52 is sequentially stored against the storage surface 38d clockwise as shown in FIG. 11D, FIG. 11C, and FIG. 11B. After the sheath 52 is contained and forms a wound circle, the more sheath 52 is contained in the sheath storing section 31 to be wound on the wound sheath 52 in another layer as shown in FIG. 11A, resulting in the completely stored sheath 52 as shown in FIG. 6 and FIG. 8.

In this way, a sheath of a treatment instrument having a predetermined elasticity is contained in the sheath storing section. An inner dimension and a depth of a recess of the sheath storing section are set in consideration of the elasticity, a diameter, and a length of the sheath. This enables an elongated sheath of a treatment instrument to be stably contained in a sheath storing section.

A storage case of this embodiment includes an extracting hole formed therein, through which a sheath of a treatment instrument having a predetermined elasticity is extracted, and a handle mounting hole formed therein, in which a handle section of the treatment instrument is mounted and also from which the sheath extends. The extracting hole and the handle mounting hole are arranged in the storage case so that the central axis of the extracting hole and the central axis of the handle mounting hole are positioned in a predetermined relationship to each other. That is, these two holes are arranged so that a direction in which the sheath is extended from the extracting hole does not coincides with a direction in which the sheath is extended from the handle section, but these two directions intersect with each other. This arrangement allows an extracted shape of the sheath, which extends downward from the storage side opening of the extracting hole to contact once the guiding plane and then extends upward to the storage surface, to be defined to be a gentle radius of curvature which curves in a constant direction.

Therefore, a pulling of the sheath contained in the sheath storing section of the storage case with a uniform pressure causes the sheath to be smoothly extracted outward, and a pushing of the sheath extracted out of the sheath storing section with a uniform pressure causes the sheath to be smoothly pushed down to be stored in a predetermined wound state.

This configuration achieves a storage case which can be manufactured at a lower cost because the sheath can be wound and contained in a sheath storing section without a rotating drum for winding the sheath in the sheath storing section.

It should be noted that reference numeral 8 in FIG. 4 designates a protective cap. The protective cap 8 may be press-fitted to an outer circumferential surface of the sheath extracting section 33. In the treatment instrument cartridge 9, the protective cap 8 mounted to the sheath extracting section 33 as shown in FIG. 7 and FIG. 8 can keep the tip end portion of the sheath 52 extended from the extracting hole 33*a* and the tissue sampling section 51 separated from the exterior environment. The treatment instrument cartridge 9 is provided to a user after sterilization with the sterilized protective cap 8 provided thereto, for example in a sterilized bag.

In assembling the treatment instrument cartridge 9, in this embodiment, the biopsy forceps 50, and the first member 34 and the second member 35 of the case body 30, all of which are already sterilized, are prepared for assembly, but these components may be first assembled into the treatment instrument cartridge 9, and then be sterilized to be put into a sterilized bag.

Now, operations of an endoscope system 1 which includes the treatment instrument cartridge 9 configured in the way described above will be explained below.

In performing a surgical operation, a staff prepares one or more treatment instrument cartridges 9 having a treatment instrument which is suitable to the purpose of the surgical operation. A staff places the treatment instrument cartridges 9 at a predetermined position in an operation room. A staff also places a coupling tube 6 having an electric advancing and retracting device 40 at one end thereof, and an operation instructing device 2 near the treatment instrument cartridge 9. It should be noted that the operation instructing device 2 is electrically connected to the controlling device 20.

At the point when an operator needs the treatment instrument, the operator informs a staff that request during an examination using an endoscope. Then the staff removes the protective cap 8 on the treatment instrument cartridge 9, which is placed in a cart (not shown), from the sheath extracting section 33, and inserts the exposed tissue sampling section 51 and the tip end portion of the sheath 52 into the housing 41 of the electric advancing and retracting device 40. After the insertion, the staff inserts the tissue sampling section 51 and the tip end portion of the sheath 52 between the rollers 43*a* and 43*b* and through a slit 42*c* in the forceps plug 42*b* to the inside of the coupling tube 6. Then the staff passes the other end of the coupling tube 6 to the operator. The operator connects the tip end of the coupling tube 6 into the opening for treatment instrument 12*b*, and operates the operation instructing device 2 at hand to introduce the sheath 52 and the like into a body cavity.

It should be noted that, when the operator introduces the sheath 52 into a body cavity, for example, air is sometimes delivered by the endoscope 10 to expand the body cavity in order to facilitate the observation of the body cavity. In this case, since the sheath 52 is inserted or retracted through the slit 42*c* in the forceps plug 42*b*, any pressure drops due to the insertion or retraction of the sheath 52 can be prevented.

In addition, since the sheath 52 is inserted or retracted through the slit 42*c* in the forceps plug 42*b*, any leak of body fluid and the like in the coupling tube 6 to the exterior environment can be prevented in the insertion or retraction of the sheath 52.

The operator locates the tissue sampling section 51 and the tip end portion of the sheath 52 in the coupling tube 6, and then operates the operation instructing device 2 to cause the rollers 43 to rotate in a predetermined direction. As the rollers 43 rotate, the sheath 52 is advanced corresponding to the rotation of the rollers 43. That is, the tissue sampling section 51 and the tip end portion of the sheath 52 is advanced through the coupling tube 6 into the treatment instrument channel 11*e* of the endoscope 10 and then is advanced through the treatment instrument channel 11*e*. The tissue sampling section 51 is extracted out of the tip end opening 11*d* at the tip end 11*a* into a body cavity. During the advancement, the sheath 52 which is wound and contained in the sheath storing section 31 of the case body 30 is extracted outward as shown in FIGS. 11A to 11D corresponding to the pushing or pulling operation of the operation instructing device 2 by the operator.

Then the operator tells the staff to operate the handle section. The staff puts his/her fingers into the finger engaging ring 54 and on the flange 55*a* at the handle section 53 to perform an operation with his/her hand which causes the tissue sampling section 51 to move from its open position into its closed position or to rotate for a tissue sampling (not shown).

After the tissue sampling is completed, the operator performs an operation with his/her hand to cause the sheath 52 to be retracted. This operation causes the rollers 43 to rotate in the direction opposite to the one described above, which makes the sheath 52 and the tissue sampling section 51 retract through the treatment instrument channel 11*e*. When the sheath 52 and the tissue sampling section 51 reach a part of the coupling tube 6 nearer the tip end thereof, the operator stops the retraction of the sheath 52. During the retraction, the sheath 52 is wound and contained in the sheath storing section 31 of the case body 30 as shown in FIGS. 11D to 11A.

Then, the operator disconnects the tip end of the coupling tube 6 from the opening for treatment instrument 12*b*. The coupling tube 6 is passed to a staff from the operator with the tissue sampling section 51 being positioned in the part of the coupling tube 6 nearer the tip end thereof. The staff draws back the tissue sampling section 51 from the coupling tube 6, and performs remained procedures on the sampled tissue in a container such as a beaker which a staff prepared beforehand. Then the staff operates the operation instructing device 2 to cause the sheath 52 to be further retracted so that the tissue sampling section 51 is disengaged from the rollers 43*a* and 43*b* in the housing 41.

After the disengagement, the staff takes away the housing 41 of the electric advancing and retracting device 40 from the sheath extracting section 33, and attaches the protective cap 8 to the sheath extracting section 33. This prevents the sheath 52 and the tissue sampling section 51 which is already inserted into the body cavity from being exposed to the exterior environment, and keeps them stored inside. It should be noted that the operation instructing device 2 may be operated by an operator or a staff according to an instruction by the operator. When a new treatment instrument is introduced into a body cavity, a treatment section of the treatment instrument and a sheath tip end portion which are disposed in a new treatment instrument cartridge 9 are introduced through the coupling tube 6, which is connected into the opening for treatment instrument 12b, into the body cavity for a treatment.

It should be noted that in this embodiment, an operator connects the coupling tube 6, to which the electric advancing and retracting device 40 is connected, into the opening for treatment instrument 12b, and then the operator inserts the tissue sampling section 51 and the tip end portion of the sheath 52 into the housing 41 of the electric advancing and retracting device 40. However, one end of the coupling tube 6, opposite to the end to which the electric advancing and retracting device 40 is connected, may be connected into the opening for treatment instrument 12b beforehand. Alternatively, the tissue sampling section 51 and the tip end portion of the sheath 52 may be inserted into the housing 41 of the electric advancing and retracting device 40 beforehand, and an operator may connect one end of the coupling tube 6, opposite to the end to which the electric advancing and retracting device 40 is connected, into the opening for treatment instrument 12b. This reduces an operator's workload.

As described above, the treatment instrument cartridge is configured by placing a treatment section of a treatment instrument, which is to be inserted through a treatment instrument channel of an endoscope, out of a storage case, storing an elongated sheath of the treatment instrument in a sheath storing section of the storage case, and placing a handle section of the treatment instrument in a treatment instrument holding section of the storage case. This configuration allows the elongated sheath of the treatment instrument to be contained in the sheath storing section in a stable state. Thus, when a treatment is performed with a treatment instrument being inserted through a treatment instrument channel of an endoscope in a surgical operation, the treatment instrument before use can be placed and left unattended in a sterile condition at a position close to an operator or in an operation room, and the treatment instrument after use can be immediately moved away from the operator and be left unattended. Even during the treatment instrument is left unattended, the sheath cannot come loose in spite of its elasticity, which eliminates any accidental hanging down of the sheath to a floor.

The treatment instrument cartridge is positioned close to an operating portion of an endoscope when the treatment section of the treatment instrument and the sheath are introduced into a treatment instrument channel of an endoscope. So the treatment section of the treatment instrument can be introduced into a body cavity with a minimum extension of the sheath outward. This surely prevents the sheath from touching a floor due to a long extension thereof, and an operator can introduce a treatment instrument of a treatment instrument cartridge into a treatment instrument channel alone by himself/herself.

The coupling tube is coupled to the opening for treatment instrument of an endoscope at one end thereof, and to the main body of the electric advancing and retracting device disposed in a sheath extracting section of a storage case at the other end thereof. This configuration enables the treatment section of a treatment instrument and the sheath which are extracted from the sheath storing section of a treatment instrument cartridge to be inserted through a treatment instrument channel via the coupling tube without any exposure to the exterior environment when the treatment instrument is introduced into a body cavity.

Therefore, there is no possibility of any scattering of unsanitary fluid when a sheath having an elasticity is withdrawn through the opening for treatment instrument of an endoscope. Therefore, in the withdrawal of a sheath, no staff needs to do the troublesome work to withdraw a sheath while covering the opening for treatment instrument with gauze.

It should be noted that in the above-described embodiment, the treatment instrument is the biopsy forceps 50, but the treatment instrument is not limited to this, and may be a high-frequency snare, a contrast tube, a basket forceps, and the like.

Figure 13:
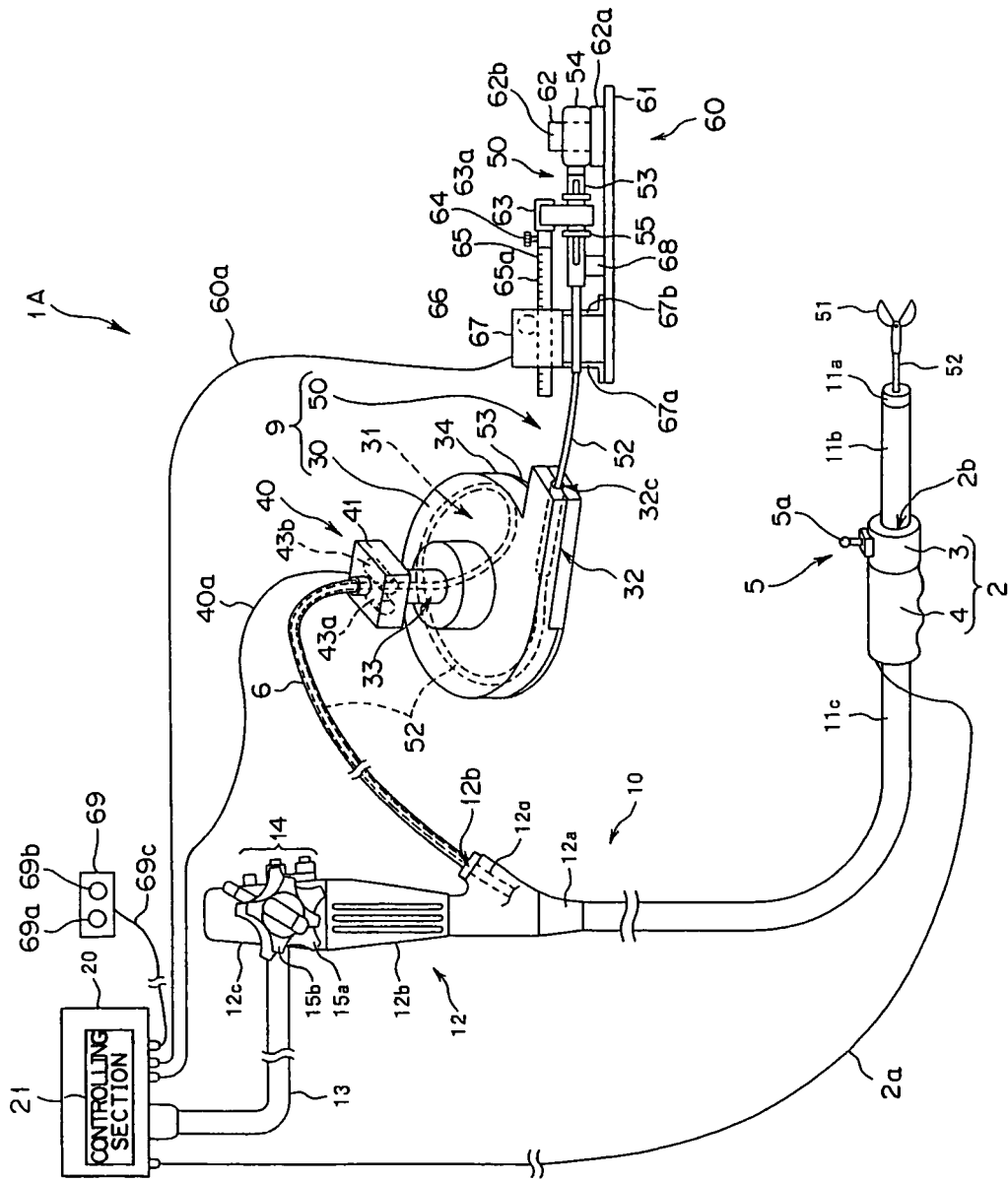
FIG. 13 is a view illustrating an entire configuration of an endoscope system according to a second embodiment.

Now, referring to FIG. 13, a second embodiment of the present invention will be explained.

An endoscope system 1A of this embodiment includes an operation instructing device 2, an endoscope 10, a controlling device 20, a treatment instrument cartridge 9 in which a sheath 52 of a treatment instrument 50 is contained in a sheath storing section 31 of a case body 30, and an electric advancing and retracting device 40 as described above, and an electric operation device 60 as well.

The electric operation device 60 includes a plate of a base body 61. The base body 61 is provided with a ring retaining section 62, a holding box 67, and a resting section 68. The holding box 67 is fixedly mounted to the base body 61 by a pair of fastening members 67a, 67b. The holding box 67 is provided with a rack 65 which has straight teeth 65a formed thereon and is movably held in forward and backward directions. A pinion gear 66a is provided in the holding box 67 which engages with the straight teeth 65a on the rack 65. The pinion gear 66a (not shown) is fixed to a shaft of a motor. With the pinion gear 66a being engaged with the straight teeth 65a on the rack 65, an operation of the motor causes the pinion gear 66a fixed to the motor shaft to rotate so that the rack 65 moves in a forward or a backward direction.

A holding section 63a is included in a slider retaining section 63 which is mounted to an end of the rack 65 by using setscrews 64. The holding section 63a of the slider retaining section 63 is disposed to hold a slider 55 of a handle section 53. Specifically, the holding section 63a holds the slider 55 so as to sandwich a body section which is located between a pair of flanges 55a on the slider 55.

The ring retaining section 62 includes a ring stand 62a and a projected section 62b. The ring stand 62a is fixed to the base body 61. The finger engaging ring 54 of the handle section 53 has the hole 54a formed therein which is arranged on the projected section 62b. This configuration makes the handle section 53 fixedly held in the electric operation device 60.

When the finger engaging ring 54 is put on the projected section 62b in the predetermined way, one side of the finger engaging ring 54 contacts the ring stand 62a. In this state, a part of the handle section 53 is rested on the resting section 68. Thus, the handle section 53 of the biopsy forceps 50 is disposed parallel to the base body 61 with a space between them.

In the above configuration, the motor is controlled, for example by a foot switch 69 which is electrically connected to the controlling device 20, to drive the rack 65 to move. That is, a driving of the motor causes the slider 55 which is held by the slider holding section 63 at the rack 65 to move forward or backward along the axis of the handle section 53. As the slider 55 moves forward or backward, an operation wire in the biopsy forceps 50 is moved to open or close the tissue sampling section 51. Specifically, an operation of a switch 69a on the foot switch 69 by an operator causes the tissue sampling section 51 to be opened, and an operation of a switch 69b on the foot switch 69 by an operator causes the tissue sampling section 51 to be closed.

It should be noted that in this embodiment, the main body 3 and the grip 4 of the operation instructing device 2 have a groove for attachment 2b formed therein. The groove for attachment 2b is formed to integrally attach the operation instructing device 2 to the inserting portion 11. As shown in FIG. 13, when the inserting portion 11 is disposed so as to engage with the groove for attachment 2b of the operation instructing device 2, the operation instructing device 2 and the inserting portion 11 are generally combined as a unit.

In this embodiment, the handle section 53 is placed on the electric operation device 60. So, the case body 30 has a sheath inserting hole 32c formed therein, instead of the handle mounting hole 32a. The sheath inserting hole 32c is a second through-hole configured to serve as a second defining section from which the sheath 52 extends in a predetermined direction. A part of the sheath 52 is fixed in the sheath inserting hole 32c to prevent any movement in an axial direction. Other configuration of the endoscope system 1A is similar to the first embodiment, and members which are the same or similar to those in the first embodiment are designated with like reference numerals, and will not be explained in detail below.

Now, operations of the endoscope system 1A configured in the way described above will be explained below.

In a surgical operation with using the endoscope system 1A, a staff prepares one or more treatment instrument cartridges 9 having a treatment instrument which is suitable to the purpose of the surgical operation. The staff places the treatment instrument cartridges 9 at a predetermined position in an operation room. The staff also places a coupling tube 6 having an electric advancing and retracting device 40 at one end thereof, an electric operation device 60, a foot switch 69, and an operation instructing device 2 near the treatment instrument cartridge 9. It should be noted that a signal cable 2a of the operation instructing device 2, a signal cable 60a of the electric operation device 60, and a signal cable 69c of the foot switch 69 are electrically connected to the controlling device 20 beforehand. A handle section of the treatment instrument, which will be used first in the surgical operation, is placed in the electric operation device 60 beforehand.

In order to use the treatment instrument during an examination using an endoscope, the operator connects the other end of the coupling tube 6 into the opening for treatment instrument 12b, as in the first embodiment. Also, the operator removes a protective cap 8 on the treatment instrument cartridge 9 from a sheath extracting section 33, and inserts the exposed tissue sampling section 51 and the tip end portion of the sheath 52 into the housing 41 of the electric advancing and retracting device 40 to place the tissue sampling section 51 and the tip end portion of the sheath 52 in the coupling tube 6.

Then the operator disposes the inserting portion 11 so as to engage with the groove for attachment 2b of the operation instructing device 2. This allows the operator to hold the operating portion by his/her one hand, and holds the operation instructing device 2 and the inserting portion 11 by the other hand.

Holding the operation instructing device 2 and the inserting portion 11, the operator manipulates the operation instructing device 2 to cause the rollers 43 to rotate in a predetermined direction. As the rollers 43 rotate, the tissue sampling section 51 and the tip end portion of the sheath 52 are advanced through the coupling tube 6 into the treatment instrument channel 11e. The tissue sampling section 51 is extracted out of the tip end opening 11d at the tip end 11a into a body cavity. During the advancement, the sheath 52 which is wound and contained in the sheath storing section 31 of the case body 30 is extracted outward as shown in FIGS. 11A to 11D.

Then the operator performs a tissue sampling. During the sampling, the operator manipulates the operation instructing device 2 to cause the tissue sampling section 51 to be advanced or retracted, and simultaneously manipulates the switches 69a and 69b of the foot switch 69 to cause the tissue sampling section 51 to be opened and closed. It should be noted that the motor for driving the rack may be controlled by an operation hand switch which is provided to the operation instructing device 2, instead of the foot switch 69.

After the tissue sampling is completed, the operator manipulates the operation instructing device 2 to cause the rollers 43 to rotate in the direction opposite to the one described above, which makes the sheath 52 and the tissue sampling section 51 retract through the treatment instrument channel 11e and the coupling tube 6. After further retraction, the tissue sampling section 51 is disengaged from the rollers 43a and 43b in the housing 41. During the retraction, the sheath 52 is wound and contained in the sheath storing section 31 as shown in FIGS. 11D to 11A.

After the disengagement, a staff takes away the housing 41 of the electric advancing and retracting device 40 from the sheath extracting section 33, and attaches the protective cap 8 to the sheath extracting section 33, and also removes the handle section 53 of the biopsy forceps 50 from the electric operation device 60. This prevents the sheath 52 and the tissue sampling section 51 which are inserted into the body cavity once from being exposed to the exterior environment, and keeps them stored inside.

When a new treatment instrument is introduced into a body cavity, a handle section of a new treatment instrument mounted in the treatment instrument cartridge 9 is placed in the electric operation device 60, and a treatment section of the treatment instrument and a sheath tip end portion of the new treatment instrument mounted in the treatment instrument cartridge 9 are introduced through the coupling tube 6, which is connected into the opening for treatment instrument 12b, into the body cavity for a treatment.

As described above, the treatment instrument cartridge is configured by extracting a treatment section of a treatment instrument, which is be inserted through a treatment instrument channel of an endoscope, outside of a storage case, storing an elongated sheath of the treatment instrument in a sheath storing section of the storage case, and placing a handle section of the treatment instrument in an electric operation device. This configuration allows an operator to introduce a treatment instrument of a treatment instrument cartridge into a treatment instrument channel, and to sample a tissue by manipulating the tissue sampling section for its opening and closing while manipulating the tissue sampling section for its advancement and retraction, alone by himself/herself. Other operations and effects of the treatment instrument cartridge are similar to those of the first embodiment.

In the above-described embodiments, the case body 30 has a sheath storing section 31 in which the sheath 52 of the biopsy forceps 50 is contained. However, the configuration of the treatment instrument cartridge is not limited to those in the embodiments, and a treatment instrument such as the sheath 52 of the biopsy forceps 50 may be contained in a case body 30A shown in FIG. 14 and FIG. 15 to form a treatment instrument cartridge 9A.

Figure 14:
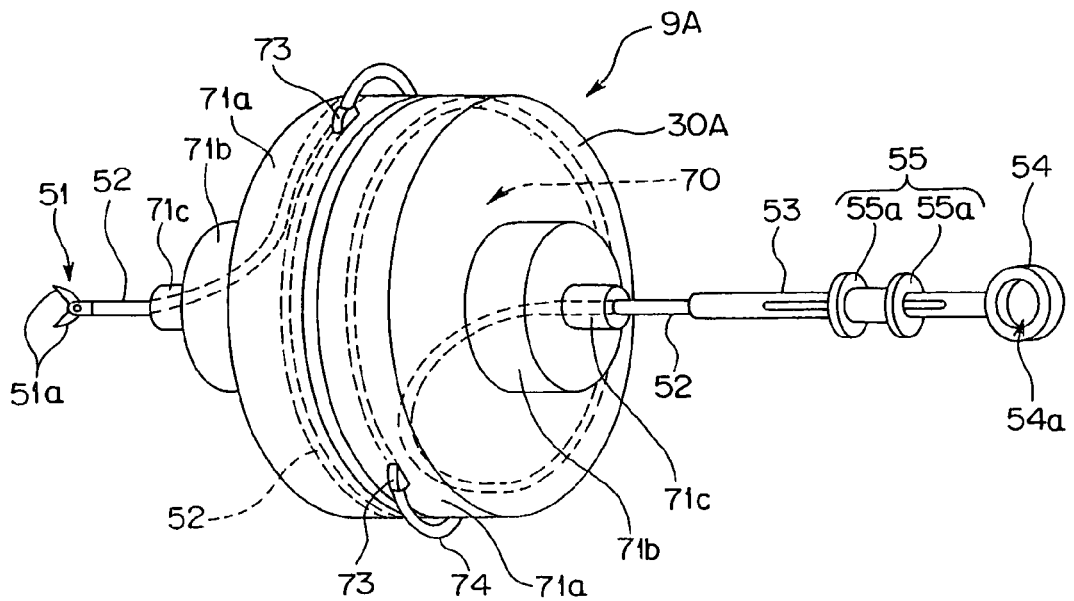
FIG. 14 is a perspective view illustrating another configuration of a storage case.
Figure 15:
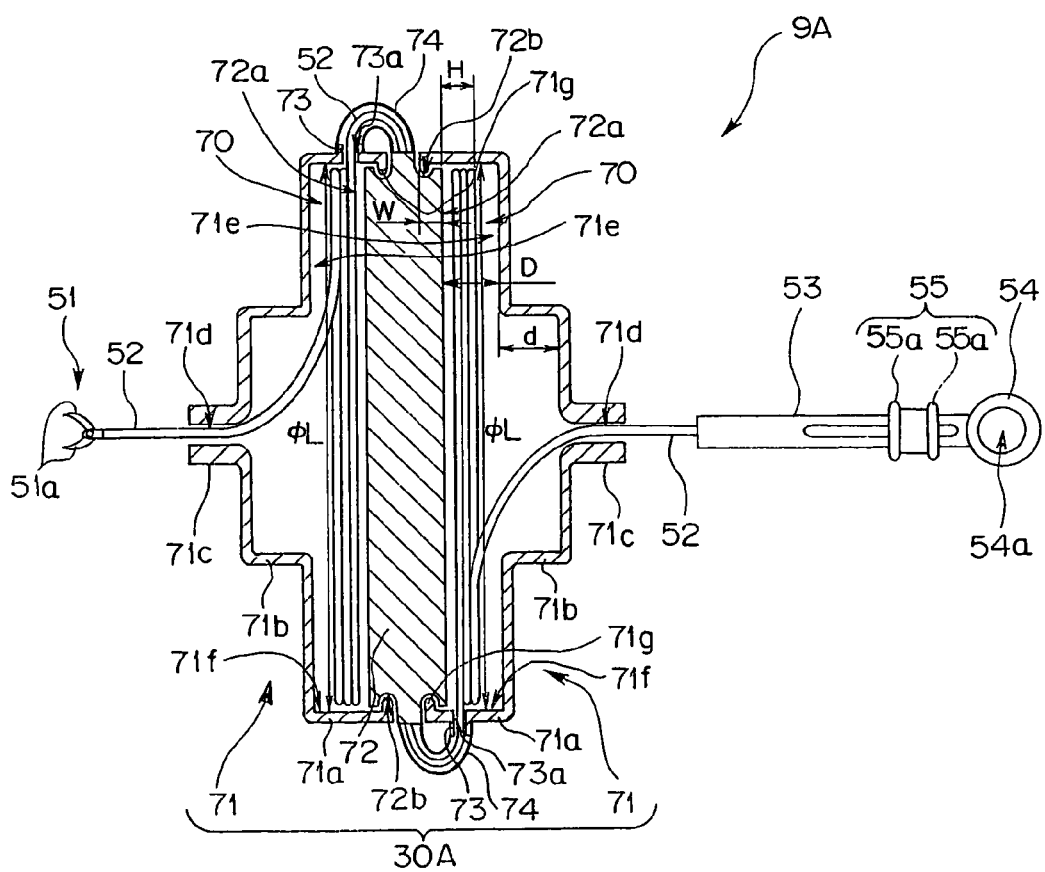
FIG. 15 is a longitudinal cross sectional view of the storage case of FIG. 14.

As shown in FIG. 14, and FIG. 15, the case body 30A of this embodiment includes a pair of sheath storing sections 70. The case body 30A includes a pair of tubular members 71, a fixing plate 72, a pair of sheath extracting sections 73, and sheath guiding tube (hereinafter, briefly referred to as a tube) 74. The tubular member 71 is made of a transparent or semi-transparent resin material. This allows an operator and the like to visually check a state of the sheath 52 in the sheath storing section 70 through the tubular member 71.

The fixing plate 72 may be a cylindrical member having a diameter the size of which is larger than a thickness thereof, and has flat surfaces, that is, guiding planes 72a against which the sheath 52 abuts. The fixing plate 72 has a pair of circumferential grooves 72b formed at its outer periphery. To the circumferential grooves 72b, an engaging section (designated by reference numeral 71g which will be explained below) on the tubular member 71 is engagedly inserted. It should be noted that the shape of the fixing plate 72 is not limited to a cylinder having a circular cross section, and may be a rectangular cylinder having a regular tetragonal cross section, regular hexagonal cross section, and the like.

The tubular member 71 is formed into a stepped shape, and has a storage space defining section 71a having a larger diameter, an extracted shape adjusting section 71b having a smaller diameter than that of the storage space defining section 71a, and a sheath extracting section 71c having a smaller diameter than that of the extracted shape adjusting section 71b. The sheath extracting section 71c has an extracting hole 71d formed therein. The extracting hole 71d is a first through-hole out of which the stored sheath 52 is extracted. It should be noted that the storage space defining section 71a has a generally same outline shape as that of the flat plate 72. In this embodiment, the storage space defining section 71a, the extracted shape adjusting section 71b, and the sheath extracting section 71c are concentrically arranged. The extracting hole 71d is positioned centrally of the sheath extracting section 71c.

The storage space defining section 71a has sheath storing sections 70 which is a recess 71e formed in the storage space defining section 71a. The recess 71e has a storage surface 71f which is the internal surface of the recess 71e, and the sheath 52 is placed in contact with the storage surface 71f. Claws 71g are provided on the internal surface of the recess 71e on the side of the opening in the storage space defining section 71a, the claws 71g serving as the engaging section and extending toward to the center of the storage space defining section 71a. The claws 71g are configured to be engagedly inserted into the circumferential groove 72b.

A diameter ϕL of the recess 71e, that is the internal dimension of the recess 71e, is determined in consideration of an elasticity and a length of the sheath 52 of the biopsy forceps 50, as described above. When the sheath 52 is stored in the recess 71e with being wound up, the elasticity of sheath 52 makes the sheath 52 unwound and stretched outward in a direction in which the winding of the sheath 52 is released, resulting in that the sheath 52 is pushed against the storage surface 71f to be in contact with the storage surface.

The recess 71e has a depth D which is determined in consideration of a diameter, a length of the sheath 52, and also a distance W between the guiding plane 72a and the circumferential groove 72b into which the claws 71g is engagedly inserted (hereinafter, referred to as an engaged width). Specifically, with the wound and laminated sheath 52 in contact with the storage surface 71f of the recess 71e, there is a relationship between a height H of the wound sheath, the depth D, and an engaged width W as follows:

$$H < D - W$$

This relationship allows the wound sheath 52 to be stably stored in the recess 71e of the sheath storing section 70.

The extracted shape adjusting section 71b has a depth d which is determined in consideration of an elasticity of the sheath 52, as described above. A specific depth d is set so that, with the sheath 52 being wound and laminated in the sheath storing section 70, when the sheath 52 at the top layer contacts the guiding plane 72a and reaches the extracting hole 71d, the sheath 52 has a shape of a curved line having a gentle radius of curvature, as described above. In this embodiment also, the tubular member 71 may include only the sheath extracting section 71c without the extracted shape adjusting section 71b.

The sheath extracting sections 73 have a defining hole 73a formed therein which is a second through-hole configured to serve as a second defining section. The defining hole 73a in the sheath extracting sections 73 defines a direction in which the sheath 52 is inserted into the sheath storing sections 70 as predetermined when the sheath 52 passes through the defining hole 73a. The sheath extracting sections 73 are integrally formed on the outer circumferential surface of the storage space defining section 71a, or formed as another member and integrally fixed on the outer circumferential surface of the storage space defining section 71a by using adhesive for example.

The tube 74 is coupled with the sheath extracting section 73 mounted to one of the tubular members 71 and the sheath extracting section 73 mounted to the other the tubular members 71. This makes the defining hole 73a in one of the sheath extracting section 73 and defining hole 73a in the other of sheath extracting section 73 in communication with each other. The tube 74 may be wound around the outer circumferential surface of the fixing plate 72.

In this embodiment, the extracting hole 71d of the case body 30A is configured to have a central axis which intersects with the guiding plane 72a at a right angle. To the contrary, the defining hole 73a is arranged so that the sheath 52, which is wound along the storage surface 71f, that is the inner surface, of the recess 71e and the guiding plane 72a, can be extended to be wound around the outer circumferential surface of the fixing plate 72 without any bending.

In this embodiment also, a plane including the central axis of the extracting hole 71d and the plane including the central axis of the defining hole 73a are arranged to intersect with each other at a right angle, while the central axis of the extracting hole 71d and the central axis of the defining hole 73a are arranged not to intersect with each other. This means the central axis of the defining hole 73a is arranged so that the plane including the central axis is parallel to the guiding plane 72a. In addition, the central axis of the defining hole 73a is arranged to be tangent to an imaginary circle around the central axis of the extracting hole 71d.

It should be noted that the pair of tubular members 71 and the fixing plate 72 are integrally fixed to each other, for example by using adhesive, with the claws 71g on the tubular members 71 being engagedly inserted into the circumferential grooves 72b of the fixing plate 72. The two tubular members 71 separated by the fixing plate 72 form the case body 30A having two sheath storing sections 70.

In the case body 30A, a predetermined length of the sheath 52 which has the tissue sampling section 51 is wound and contained in one of the sheath storing sections 70, while a predetermined length of the sheath 52 which has the handle section 53 is wound and contained in the other sheath storing section 70. It should be noted that, to prevent any change of the sheath length of the sheath 52 contained in each of the sheath storing sections 70 in the case body 30A, a sheath fixing section may be provided in the tube 74 to restrain the movement of the sheath 52.

In this way, in this embodiment, the tissue sampling section 51 can be extracted, and also the handle section 53 can be placed at any position with a suitable length of the sheath 52 in one of the sheath storing sections 70 being extracted, as described above.

A length of the sheath 52 contained in one of the sheath storing sections 70 and a length of the sheath 52 contained in the other sheath storing section 70 can be adjusted as needed so that an extended length of the tissue sampling section 51 is changed.

As described above, the cartridge in this embodiment has two sheath storing sections. Into one of the sheath storing sections, a length of the sheath is wound and contained in consideration of how far the tissue sampling section is introduced into a body cavity, and into the other sheath storing section, a length of the sheath is wound and contained in order to allow a handle section of the sheath to move. This configuration enables an adjustment of an extracted length of the tissue sampling section as needed for a medical procedure. Also, a handle section of a treatment instrument can be placed at a position desired by an operator or the like for a medical procedure by extracting the sheath contained in the other sheath storing section.

Other operations and effects of the treatment instrument cartridge are similar to those of the above-described embodiment.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope system, comprising:
an endoscope including an inserting portion which has a treatment instrument channel formed therein;
a treatment instrument cartridge, comprising:
a treatment instrument, including: a treatment instrument inserting portion which is inserted through the treatment instrument channel of the endoscope and has a predetermined elasticity; a treatment section which forms a tip end of the treatment instrument inserting portion; and an operating portion which is provided at a base end of the treatment instrument inserting portion and operates the treatment section; and
a storage case, including: an inserting portion storing section having an inside surface for winding and containing the treatment instrument inserting portion; a first defining section having a first through-hole in communication with the inserting portion storing section and the exterior for defining a direction in which a part of the treatment instrument inserting portion nearer one end thereof contained in the inserting portion storing section is extracted to the exterior; a second defining section having a second through-hole in communication with the inserting portion storing section and the exterior for defining a direction in which a part of the treatment instrument inserting portion nearer the other end thereof contained in the inserting portion storing section is extracted to the exterior; a guiding plane which is provided between the first defining section and the second defining section, positioned to intersect with the central axis of the first through-hole at a right angle, and is a plane against which the treatment instrument inserting portion is pushed; and a storage surface which is provided between the first defining section and the second defining section, extends in a vertical direction from the guiding plane, and is the inside surface for placing the treatment instrument inserting portion in contact therewith due to an elasticity of the treatment instrument inserting portion;
an advancing and retracting device which has a driving power source for providing a driving power, and is provided between the treatment instrument inserting channel of the endoscope and the first through-hole to extract the treatment instrument inserting portion extended from the first through-hole out of the first through-hole and to push the treatment instrument inserting portion into the first through-hole;
a controlling device electrically connected to the driving power source for controlling an operation of the driving power source; and
an operation instructing device for issuing an instruction on an operation of the driving power source to the controlling device.

2. The endoscope system according to claim 1, wherein a central axis of the first through-hole and a central axis of the second through-hole do not intersect with each other, and a plane including the central axis of the first though-hole and a plane including the central axis of the second through-hole intersect with each other at a right angle.

3. The endoscope system according to claim 2, wherein the first defining section is positioned centrally of the inserting portion storing section, and the second defining section is positioned relative to the outer circumferential surface of the inserting portion storing section.

4. The endoscope system according to claim 3, wherein the central axis of the second through-hole in the second defining section is parallel to a line tangent to the outer circumferential surface of the inserting portion storing section.

5. The endoscope system according to claim 1, wherein the second defining section further comprises an operating portion holding section for holding the operating portion of the treatment instrument.

6. The endoscope system according to claim 5, wherein the operating portion holding section holds the operating portion of the treatment instrument which is fitted therein with play.

7. A treatment instrument cartridge, comprising:
a treatment instrument, including: an treatment instrument inserting portion which is inserted through a treatment instrument channel of an endoscope and has a predetermined elasticity; a treatment section which forms a tip end of the treatment instrument inserting portion; and an operating portion which is provided at a base end of the treatment instrument inserting portion and operates the treatment section; and
a storage case, including: an inserting portion storing section having an inside surface for winding and containing the treatment instrument inserting portion; a first defining section having a first through-hole in communication with the inserting portion storing section and the exterior for defining a direction in which a part of the treatment instrument inserting portion nearer one end thereof contained in the inserting portion storing section is extracted to the exterior; a guiding plane for guiding the treatment instrument inserting portion in a predetermined direction, the guiding plane being positioned to intersect with the central axis of the first through-hole at a right angle, and being a plane against which the treatment instrument inserting portion inserted through the first through-hole is pushed; a storage surface which extends in a vertical direction from the guiding plane, and is the inside surface for winding and containing the treatment instrument inserting portion guided by the guiding plane in contact with the surface due to elasticity of the treatment instrument inserting portion; a second defining section having a second through-hole for communicating the treatment instrument inserting portion and the exterior and for defining a direction in which the other end side of the treatment instrument inserting portion wound and contained by the storage surface is extracted to the exterior; and a holding section in communication with the second through-hole, for holding the operating portion provided at the other end side of the treatment instrument inserting portion.

8. The treatment instrument cartridge according to claim 7, wherein a central axis of the second through-hole in communication with the holding section is parallel to a line tangent to the outer circumferential surface of the inserting portion storing section.

9. The treatment instrument cartridge according to claim 7, wherein a central axis of the first through-hole and a central axis of a second through-hole in communication with the holding section do not intersect with each other, and a plane including the central axis of the first through-hole and a plane including the central axis of the second through-hole intersect with each other at a right angle.

10. The treatment instrument cartridge according to claim 7, wherein the holding section holds the operating portion of the treatment instrument which is fitted therein with play.

11. The treatment instrument cartridge according to claim 7, wherein the holding section has a section for rotatable holding in a form of a groove or projection, and the operating portion has a projected section for the groove or a recess for the projection.

12. The treatment instrument cartridge according to claim 7, further comprising, a protective cover for covering a tip end of the treatment instrument inserting portion which is extracted from the first through-hole.

13. A storage case, comprising:
an inserting portion storing section having an inside surface for winding and containing the treatment instrument inserting portion;
a first defining section having a first through-hole in communication with the inserting portion storing section and the exterior for defining a direction in which a part of the treatment instrument inserting portion nearer one end thereof contained in the inserting portion storing section is extracted to the exterior;
a guiding plane for guiding the treatment instrument inserting portion into a predetermined direction, the guiding plane being positioned to intersect with the central axis of the first through-hole at a right angle and being a plane against which the treatment instrument inserting portion inserted through the first through-hole is pushed;
a storage surface extending in a vertical direction from the guiding plane, the storage surface being an inside surface for winding and containing the treatment instrument inserting portion guided by the guiding plane in contact with the surface due to elasticity of the treatment instrument inserting portion;
a second defining section having a second through-hole for communicating the treatment instrument inserting portion and the exterior and for defining a direction in which the other end side of the treatment instrument inserting portion wound and contained by the storage surface is extracted to the exterior; and
a holding section in communication with the second through-hole, for holding the operating portion provided at the other end side of the treatment instrument inserting portion.

14. The storage case according to claim 13, wherein a central axis of the second through-hole in communication with the holding section is parallel to a line tangent to an outer circumferential surface of the inserting portion storing section.

15. The storage case according to claim 13, wherein a central axis of the first through-hole and a central axis of the second through-hole in communication with the holding section do not intersect with each other, and a plane including the central axis of the first through-hole and a plane including the central axis of the through-hole in the holding section intersect with each other at a right angle.

16. The storage case according to claim 13, wherein the holding section holds the operating portion of the treatment instrument which is fitted therein with play.

17. The storage case according to claim 13, wherein the holding section has a section for rotatable holding in a form of a groove or projection, and the operating portion has a projected section for the groove or a recess for the projection.

* * * * *